(12) United States Patent
Araki et al.

(10) Patent No.: US 8,535,932 B2
(45) Date of Patent: Sep. 17, 2013

(54) LECANICILLIUM MUSCARIUM STRAIN V-5, PEST EXTERMINATION METHOD USING THE SAME, AND MICROORGANISM PESTICIDE COMPRISING THE SAME

(75) Inventors: Satoshi Araki, Shiga (JP); Munekazu Ogawa, Shiga (JP); Takayuki Kashima, Shiga (JP)

(73) Assignee: Ishihara Sangyo Kaisha, Ltd, Osaka (JP)

( * ) Notice: Subject to any disclaimer, the term of this patent is extended or adjusted under 35 U.S.C. 154(b) by 165 days.

(21) Appl. No.: 13/058,366

(22) PCT Filed: Aug. 11, 2009

(86) PCT No.: PCT/JP2009/064197
§ 371 (c)(1),
(2), (4) Date: Feb. 10, 2011

(87) PCT Pub. No.: WO2010/018830
PCT Pub. Date: Feb. 18, 2010

(65) Prior Publication Data
US 2011/0135609 A1     Jun. 9, 2011

(30) Foreign Application Priority Data

Aug. 11, 2008 (JP) .................................. 2008-206866

(51) Int. Cl.
*C12N 1/20* (2006.01)
(52) U.S. Cl.
USPC ........ 435/254.1; 424/93.5; 435/171; 504/117
(58) Field of Classification Search
None
See application file for complete search history.

(56) References Cited

FOREIGN PATENT DOCUMENTS

| JP | 2003-335612 A | 11/2003 |
| JP | 2008-061530 A | 3/2008 |

OTHER PUBLICATIONS

Cuthbertson et al., Mycopathologia. Aug. 2005;160(1):35-41.*
Talwar, B.H., Thesis, University of Agriculturla Sciences, Dharwad, Dec. 2005 (http://etd.uasd.edu/ft/th8579.pdf), accessed Dec. 13, 2012.*

International Search Report, dated Nov. 24, 2009, issued in Application No. PCT/JP2009/064197.
Tsutomu Saito, Biseibutsu Noyaku (*Verticillium lecanii* Seizai) ni yoru Shisetsu Gaichu no Bojo:, Kongetsu no Nogyo, 2001, pp. 72-77.
Andrew Cuthbertson, et al. "Compatibility of the entomopathogenic fungus *Lecanicillium muscarium* and insecticides for eradication of the sweetpotato whitefly, *Bemisia tabaci*", Mycopathologia, 2005, vol. 160, pp. 35-41.
Liande Wang, et al. "Toxicity and feeding deterrence of crude toxin extract of *Lecanicillium* (*Verticillium*) *lecanii* (*Hyphomycetes*) against sweet potato whitefly, *Bemisia tabaci* (Homoptera: Aleyrodidae)", Pest Management Science, 2007, vol. 63, pp. 381-387.
Andrew Cuthbertson,et al. "Further compatibility tests of the entomopathogenic fungus *Lecanicillium muscarium* with conventional insecticide products for control of sweetpotato whitefly, *Bemisia tabaci* on poinsettia plants", Insect Science, 2008, vol. 15, pp. 355-360.
Vassili Kouvelis, et al. "The analysis of the complete mitochondrial genome of *Lecanicillium muscarium* (synonym *Verticillium lecanii*) suggests a minimum common gene organization in mtDNAs of Sordariomycetes; phylogenetic implications," Fungal Genetics and Biology, 2004, vol. 41, pp. 930-940.
Aiuchi, D. et., al. "Screening of *Verticillium lecanii* (*Lecanicillium* spp.) Hybrid Strains Based on Evolution of Pathogenicity Against Cotton Aphid and Greenhouse Whitefly, and Viability on the Leaf Surface", Japanese Journal of Applied Entomology and Zoology, vol. 51, No. 3, Jan. 1, 2007, pp. 205-212.
Extended European Search Report issued on Dec. 9, 2011 by the European Patent Office in the corresponding European Patent Application No. 09806721.8.
Japanese Patent Office, Communication dated Jun. 4, 2013, issued in a counterpart application No. 2010-524733.

* cited by examiner

*Primary Examiner* — Irene Marx
(74) *Attorney, Agent, or Firm* — Sughrue Mion, PLLC

(57) ABSTRACT

A microbial pesticide which is safe for the environment, fast-acting and excellent in an insecticidal effect in case of spray treatment for eggs and larvae of a pest is required. The invention provides a method for controlling at least one pest selected from the group consisting of whiteflies, aphid, spider mites, thrips, rust mites, leaf miners, pyralidae, cabbage moths and longhorn beetles, with *Lecanicillium muscarium* strain V-5 (deposition number: FERM BP-11135); and a microbial pesticide comprising the strain.

4 Claims, 2 Drawing Sheets

LECANICILLIUM MUSCARIUM STRAIN V-5, PEST EXTERMINATION METHOD USING THE SAME, AND MICROORGANISM PESTICIDE COMPRISING THE SAME

TECHNICAL FIELD

This invention relates to a *Lecanicillium muscarium* strain V-5, a pest control method with the same and a microbial pesticide comprising the same. The invention is made for controlling a pest environment-friendly, quickly and for a long of time, particularly in the field of agriculture and horticulture.

BACKGROUND OF THE INVENTION

Some filamentous fungi are natural enemies of insects and mites, and for example, natural enemy filamentous fungi belonging to the genus *Verticillium* and the genus *Beauveria* have been put into practical use as insecticides. Some strains which were classified as *Verticillium lecani* in past days have been recently reclassified into the genus *Lecanicillium* based on the morphological observation of conidia and phialide and β-tubulin gene restriction fragment length polymorphism analysis. As a result, the strain of the invention and trade name MYCOTAL (manufactured by KOPPERT) were reclassified into *Lecanicillium muscarium*. Patent Literature 1 discloses a microbial pesticide having a green plant surface adherence property which comprises a strain of *Verticillium lecani* having an adherence activity to a green plant surface as an entomopathogenic fungus, but there is no description on the strain of the invention. In addition, as an insecticidal microbial pesticide comprising *Lecanicillium muscarium*, MYCOTAL is on the market as a *Verticillium lecani* wettable powder, but colony of the strain of the invention is different from that of the strain included in MYCOTAL.

CITATION LIST

Patent Literature

Patent Literature 1: JP-A-2003-335612

SUMMARY OF INVENTION

Technical Problem

The technical problem of the invention is to provide a new strain of a filamentous fungus which is useful as a microbial pesticide which is safe for the environment, fast-acting and excellent in an insecticidal effect in case of spray treatment for eggs and larvae of a pest.

Solution to Problem

With the aim of solving the above described problems, the present inventors have found the strain of the invention which exhibits higher mortality of an objective pest and can control the objective pest within a shorter period of time than the conventionally known filamentous fungi belonging to *Lecanicillium muscarium*. That is, the invention relates to a *Lecanicillium muscarium* strain V-5 (deposition number: FERM BP-11135), a pest control method using the strain and a microbial pesticide comprising the strain.

(Isolation and Deposition Application of *Lecanicillium Muscarium* Strain V-5)

The *Lecanicillium muscarium* strain V-5 of the invention (hereinafter referred to as the strain of the invention) is a strain isolated from silver leaf whitefly in a greenhouse of ISHIHARA SANGYO KAISHA, LTD., CENTRAL RESEARCH INSTITUTE (2-3-1, Nishishibukawa, Kusatsu, Shiga, Japan). The strain of the invention was identified as *Lecanicillium muscarium* according to the classification by R. Zare and W. Gams et al. (Nova Hedwigia 73: 1-50, 2001), based on its morphological properties (whorls of awl-shaped phialide are formed on the conidiophore and single conidia are formed on its tip in a lump, length of the phialide is from 11.2 µm to 34.3 µm, diameter of the base is from 1.1 µm to 2.7 µm, the conidium is an oval or club shape and its size is from 1.4 µm to 3.4 µm×from 2.1 µm to 7.5 µm, the colony is from white to yellowish white, and formation of secondary phialide is not observed) and on the result of restriction fragment length polymorphism of β-tubulin gene (a DNA fragment of 540 bp was amplified by PCR and fragments of 360 bp and 180 bp were formed by HaeIII digestion). The strain of the invention deposited as *Lecanicillium muscarium* strain V-5 (deposition number: FERM BP-11135) in National Institute of Advanced Industrial Science and Technology, International Patent Organism Depositary (Chuo 6, 1-1-1, Higashi, Tsukuba, Ibaraki, Japan) and received by the center on Jun. 10, 2009. It is a filamentous fungus which has insecticidal and acaricidal actions, and a microbial pesticide comprising this strain is useful in controlling a pest.

Advantageous Effects of Invention

When the strain of the invention is used, pests can be controlled markedly efficiently. Since the strain of the invention is excellent in propagation ability, it can ensure a high cell concentration and also maintain an excellent insecticidal effect. Based on this, efficient pest control becomes possible. Also, since it exhibits the insecticidal effect on the egg stage of pests, it becomes possible to carry out efficient pest control at early stage. In addition, since the invention uses a filamentous fungus, it also has a markedly high safety for the environment and is also useful in the case of controlling a pest for which fast-acting property and sustained effect are required.

DESCRIPTION OF EMBODIMENTS

Figure 1:
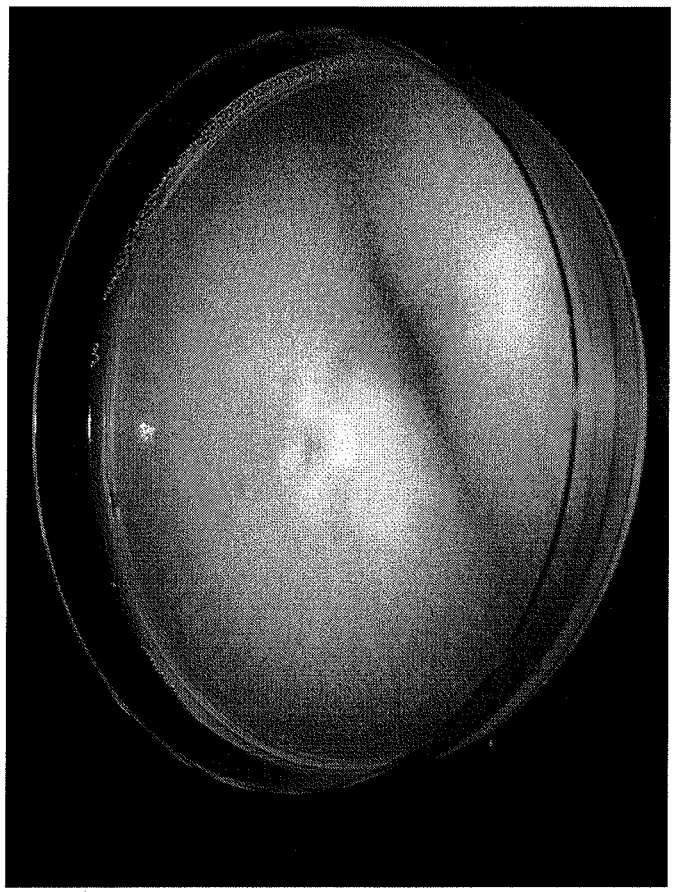
FIG. 1 A photograph showing a colony of the strain of the invention in Test Example 3.

The strain of the invention can be used as a microbial pesticide by applying it as it is or after optionally diluting with water. Its concentration of application and amount of application vary depending on various conditions such as kind of a pest, growing stage of a pest and weather condition, but the amount of application is generally from $5\times10^6$ spores to $5\times10^{12}$ spores, preferably from $5\times10^7$ spores to $5\times10^{11}$ spores, as the number of spores of the strain of the invention per 1 are.

The strain of the invention can be used as a microbial pesticide by making it into a formulation. In preparing the formulation, a general method for formulating an insect pathogen as a microbial pesticide can be used. If necessary, it can be formulated into a shape such as a dust, a wettable powder, a suspension and an oil flowable by optionally combining with a carrier (for example, a solid carrier and a liquid carrier), a surfactant, other formulation adjuvants and the like. Among these, a preferable shape is a wettable powder which is firstly made into a dust and then dissolved in water to spray before use. When the strain of the invention is made into a wettable powder and used by diluting with water, the strain is applied after diluting the wettable powder in such a manner that density of the strain of the invention becomes generally from $10^2$ spores to $10^{10}$ spores per 1 ml, preferably from $10^3$ spores to $10^8$ spores per 1 ml in terms of the number of spores in the application solution.

Examples of the solid carriers include diatomaceous earth, calcium hydroxide, calcium carbonate, talc, white carbon, kaoline, bentonite, kaolinite, mixture of sericite, clay, sodium carbonate, sodium hydrogencarbonate, sodium sulfate, zeolite and starch. In addition, examples of the liquid carriers include solvents such as water, toluene, xylene, solvent naphtha, dioxane, acetone, isophorone, methyl isobutyl ketone, chlorobenzene, cyclohexane, dimethyl sulfoxide, dimethylformamide, dimethylacetamide, N-methyl-2-pyrrolidone, and alcohol; vegetable oils and mineral oils such as olive oil, kapok oil, castor oil, palm oil, camellia oil, coconut oil, sesame oil, corn oil, rice bran oil, peanut oil, cotton seed oil, soybean oil, rape seed oil, linseed oil, tung oil and liquid paraffins; and the like.

Examples of the surfactants includes anionic surfactants, such as a salt of fatty acid, a benzoate, an alkylsulfosuccinate, a dialkylsulfosuccinate, a polycarboxylate, a salt of alkylsulfuric acid ester, an alkyl sulfate, an alkylaryl sulfate, an alkyl diglycol ether sulfate, a salt of alcohol sulfuric acid ester, an alkyl sulfonate, an alkylaryl sulfonate, an aryl sulfonate, a lignin sulfonate, an alkyldiphenyl ether disulfonate, a polystyrene sulfonate, a salt of alkylphosphoric acid ester, an alkylaryl phosphate, a styrylaryl phosphate, a salt of polyoxyethylene alkyl ether sulfuric acid ester, a polyoxyethylene alkylaryl ether sulfate, a salt of polyoxyethylene alkylaryl ether sulfuric acid ester, a polyoxyethylene alkyl ether phosphate, a salt of polyoxyethylene alkylaryl phosphoric acid ester, and a salt of a condensate of naphthalene sulfonate with formalin; nonionic surfactants, such as a sorbitan fatty acid ester, a glycerin fatty acid ester, a fatty acid polyglyceride, a fatty acid alcohol polyglycol ether, acetylene glycol, acetylene alcohol, an oxyalkylene block polymer, a polyoxyethylene alkyl ether, a polyoxyethylene alkylaryl ether, a polyoxyethylene styrylaryl ether, a polyoxyethylene glycol alkyl ether, a polyoxyethylene fatty acid ester, a polyoxyethylene sorbitan fatty acid ester, a polyoxyethylene glycerin fatty acid ester, a polyoxyethylene hydrogenated castor oil and a polyoxyethylene fatty acid ester; and the like. These surfactants can improve dispersibility and spreading property of a fungus body at the time of spraying.

Examples of the other formulation adjuvants include an emulsifying agent, a dispersing agent, a stabilizer, a moistening agent, a suspension agent, a spreader, a penetrating agent, a fungicide and the like. Examples of the emulsifying agent include lignin sulfonate, alginate and the like. Examples of the dispersing agent include polyvinyl alcohol, gum arabic, carboxymethylcellulose and the like. Examples of the stabilizer include acid isopropyl phosphate, polyoxyethylene resin acid (ester), an abietic acid salt and the like. Examples of the moistening agent include dinaphthyl methane disulfonate and the like.

In the method for controlling a pest using the strain of the invention, the drug is applied by spraying it on a pest, a habitat of the pest, a plant to be protected from the pest, and the like, using a sprayer such as a power sprayer, a hanging type sprayer, a hand sprayer, if necessary. In addition, in carrying out the application, it can be applied by mixing with other insecticide and acaricide which do not exhibit bad influences on natural enemy filamentous fungi as well as a fertilizer, a bactericide, a plant growth regulator and the like.

Examples of the pest to be controlled by the pest control method of the invention include whiteflies, such as *Trialeurodes vaporariorum, Bemisia tabaci* and *Dialeurodes citri*; aphid, such as *Myzus persicae, Aphis gossypii, Brevicoryne brassicae, Aulacorthum solani, Lipaphis erysimi, Macrosiphum euphorbiae* and *Neotoxoptera formosana*; spider mites, such as *Panonychus citri, Panonychus ulmi, Tetranychus urticae* and *Tetranychus kanzawai*; thrips, such as *Frankliniella intonsa, Frankliniella occidentalis, Thrips palmi* and *Scirtothrips dorsalis*; rust mites, such as *Aculops pelekassi* and *Aculops lycopersici*; leaf miners, such as *Liriomyza trifolii*; Pyralidae; cabbage moth; longhorn beetles, such as *Anoplophora malasiaca* and *Phytoecia rufiventris*; and the like. Preferable examples of the pest to be controlled include whiteflies, thrips and the like. In addition, examples of the plants to be protected from these pests include fruit trees, such as oranges, apples, pears, peaches, grapes, figs, and cherry fruits; tea; vegetables, such as eggplants, cucumbers, tomatos, spinach, cabbages and parsley; fruits, such as strawberries, melons and watermelons; flowering trees, such as roses, chrysanthemums, carnations, cherries and camellias; foliage plants, such as begonias; and the like.

A mutant strain obtained through natural or induced mutation using the strain of the invention as a parent strain is also included in the strain of the invention as long as it has the same character as the strain of the invention. Examples of the method for preparing these mutant strains include a conventionally known method, such as a method in which a parent strain is subjected to an artificial mutation treatment with a mutagen such as ultraviolet ray irradiation and nitrosoguanidine (NTG) and then a strain having excellent insecticidal effect is selected.

Next, specific embodiments of the invention are described, but the invention should not be limited to these embodiments.
(1) A method for controlling a pest, comprising treating a pest with the strain of the invention.
(2) The method described in (1), wherein the pest is at least one species selected from the group consisting of whiteflies, aphid, spider mites, thrips, rust mites, leaf miners, pyralidae, Cabbage Moth and longhorn beetle.
(3) The method described in (1), wherein the pest is whiteflies.
(4) The method described in (1), wherein the pest is thrips.

EXAMPLES

Test Example 1

Spraying Test on Egg of *Bemisia tabaci*

Test Methods (1) Four pots having a diameter of 7 cm in which a one leaf stage cucumber (variety: Hokushin) was planted were put in an insect case (260×340×340 mm) and adults of *Bemisia tabaci* type B were allowed to lay eggs for 7 hours. Each pot in which eggs were laid in this manner was transferred into an insect room maintained at 25° C. under dark conditions for 8 hours per day and left to stand to grow whitefly. Five days after the oviposition (*Bemisia tabaci*: egg stage), the number of eggs laid on the cucumber leaves was recorded.

(2) Using a spray gun, a spraying liquid which had been diluted and adjusted to a given concentration (conidia suspension, within 2 hours after preparation) was sprayed once on the foliage parts on each pot in such a manner that the amount of sprayed water became 50 ml per 4 pots. Immediately after the spraying, they were transferred into a lidded plastic container (kept at 100% humidity, the bottom part was filled with water) and allowed to stand still for 15 hours at 25° C. under dark conditions. Thereafter, the cucumber leaves were left to stand in insects rooms under the same conditions as (1).

(3) Using a stereoscopic microscope, life or death of *Bemisia tabaci* was judged to calculate the death rate 7 days (*Bemisia tabaci*: 1 and 2 instar larval stages), 13 days (*Bemisia tabaci*: 2 and 3 instar larval stages), 19 days (*Bemisia tabaci*: 4 instar larval stage) and 26 days (*Bemisia tabaci*: post-emergence stage) after the spraying treatment of the drug liquid. In this connection, for the sake of comparison, a test was also carried out using a spraying liquid prepared by diluting the aforementioned trade name MYCOTAL (manufactured by KOPPERT) to give a conidia concentration of $3.0 \times 10^6$/ml which is a practical concentration. The test results are shown in Table 1.

Test Results

TABLE 1

| Test strains | Spraying concentration (conidia/ml) | Death rate (%) | | | |
|---|---|---|---|---|---|
| | | After 7 days | After 13 days | After 19 days | After 26 days |
| Strain of the invention | $3.0 \times 10^6$ | 4 | 67 | 78 | 80 |
| Strain of the invention | $3.0 \times 10^7$ | 7 | 89 | 97 | 98 |
| MYCOTAL | $3.0 \times 10^6$ | 5 | 19 | 24 | 28 |
| No treatment | 0 | 6 | 18 | 21 | 24 |

Test Example 2

Spraying Test to *Bemisia tabaci* Larvae)

Test Methods (1) Five pots having a diameter of 7 cm in which a one leaf stage cucumber (variety: Hokushin) was planted were put in an insect case (260×340×340 mm) and adults of *Bemisia tabaci* type B were allowed to lay egg for 7 hours. Each pot in which eggs were laid in this manner was transferred into an insect room maintained at 25° C. under dark conditions for 8 hours per day and left to stand to grow whitefly. Ten days after the oviposition (*Bemisia tabaci*: 1 and 2 instar larval stages), the number of eggs living on the cucumber leaves was recorded.

(2) Using a spray gun, a spraying liquid which was diluted and adjusted to a given concentration (conidia suspension, within 2 hours after preparation) was sprayed once on the foliage parts on each pot in such a manner that the amount of sprayed water became 50 ml per 5 pots. Immediately after the spraying, they were transferred into a lidded plastic container (kept at 100% humidity, the bottom part was filled with water) and left to stand for 15 hours at 25° C. under dark conditions. Thereafter, the cucumber leaves were left to stand in insects rooms under the same conditions as (1).

(3) Using a stereoscopic microscope, life or death of *Bemisia tabaci* was judged to calculate the death rate 8 days (*Bemisia tabaci*: 2 and 3 instar larval stages), 14 days (*Bemisia tabaci*: 3 and 4 instar larval stages), 17 days (*Bemisia tabaci*: 4 instar larval stage to post-emergence) and 21 days (*Bemisia tabaci*: post-emergence) after the spraying treatment of the liquid. In this connection, for the sake of comparison, a test was also carried out using a spraying liquid prepared by diluting the aforementioned trade name MYCOTAL (manufactured by KOPPERT) to give a conidia concentration of $1.0 \times 10^6$/ml which is a practical concentration. The test results are shown in Table 2.

Test Results

TABLE 2

| Test strains | Spraying concentration (conidia/ml) | Death rate (%) | | | |
|---|---|---|---|---|---|
| | | After 8 days | After 14 days | After 17 days | After 21 days |
| Strain of the invention | $1.0 \times 10^6$ | 68 | 95 | 98 | 98 |
| Strain of the invention | $1.0 \times 10^7$ | 92 | 100 | 100 | 100 |
| MYCOTAL wettable powder | $1.0 \times 10^6$ | 17 | 25 | 28 | 28 |
| No treatment | 0 | 8 | 10 | 11 | 11 |

Test Example 3

Comparison of Forms of Colonies Between the Strain of the Invention and Existent Strain (1) Preparation of Potato Saccharose Agar Medium (Hereinafter Referred to as PSA)

200 g of peeled potato was boiled in ion exchange water, and the boiled broth was filtered through four-folded gauze. To the filtered potato broth, 20 g of saccharose and 15 g of agar were added, followed by further boiling to dissolve saccharose and agar. After adjusting the volume to 1 liter, the obtained solution was subjected to a sterilization treatment at 121° C. for 20 minutes using an autoclave to prepare PSA. Thereafter, 20 ml of PSA was dispensed into sterilized Petri dishes (86 mm in diameter) in a clean bench to prepare the PSA medium.

(2) Culturing of Strains

A small amount of each strain was inoculated on a central position of the PSA medium and subjected to static culturing in a constant temperature chamber of 25° C. under dark conditions for 8 hours per day. The situations of the colony were in time-course observed and taken a picture 28 days after inoculation. As the strains, the strain of the invention and a strain isolated from MYCOTAL were used.

(3) Results

Figure 2:
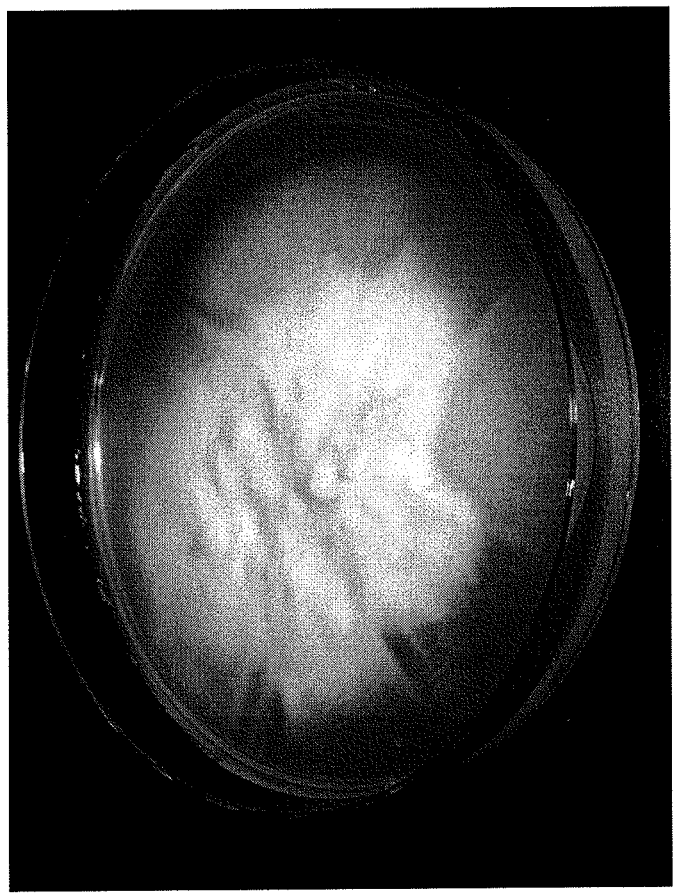
FIG. 2 A photograph showing a colony of a strain isolated from MYCOTAL in Test Example 3.

As shown in FIG. 1, the colony of the strain of the invention did not show a significant difference between its central part and peripheral part and uniformly spread out as a whole. On the other hand, as shown in FIG. 2, the central part of the colony of strain isolated from MYCOTAL was three-dimensionally swollen and peripheral part of the colony was flat. In such a manner, both strains formed clearly different colonies.

Test Example 4

Comparative Test between the Strain of the Invention and Existent Strain (1) PSA medium was prepared by dispensing 20 ml of PSA into sterilized Petri dishes (86 mm in diameter) in a clean bench in the same way as in Test Example 3. To the PSA medium, 0.5 ml of a diluted and adjusted conidia suspension (containing about 5 conidia) was inoculated dropwise in such a manner that they were uniformly distributed as a whole and then cultured statistically in a constant temperature chamber of 25° C. under dark conditions for 8 hours per day to form colonies. As the conidia suspension, the conidia suspensions of the strain of the invention and the strain isolated from MYCOTAL were used.

(2) Two weeks after inoculation, the radius of the colony formed by mono conidium was measured, and each colony with agar was cut out from medium using a surgical knife. A quarter of the cut out colony was transferred into a small Petri dish (4 cm in diameter) filled with 3 ml of ion exchange water to wash away the conidia. Further, the conidia adhered to the cut out agar were again washed away using 2 ml of ion exchange water. In this manner, 5 ml of a conidia wash liquid was obtained. Into a test tube, 0.5 ml of the obtained conidia wash liquid was dispensed, diluted with 4.5 ml of ion exchange water and thoroughly mixed using a Vortex mixer to prepare a test liquid for counting the number of conidia.

(3) The test liquid for counting the number of conidia was dropped on a counting chamber, the number of conidia was counted under a microscope and the number of total conidia on the medium surface was calculated. The results were shown in Table 3. In this connection, the test liquid for counting the number of conidia was dropped on the counting chamber after diluting it to such a concentration that the number of conidia can be counted, if necessary. Also, the test was carried out 5 times, and the average values were shown as a result.

TABLE 3

Radiuses of colony formed from one conidium and concentration of conidia (after 2 weeks)

| Test strains | Colony radiuses (cm) | Total number of conidia in colony (conidia) | Conidia concentration in colony (conidia/cm$^2$) |
|---|---|---|---|
| Strain of the invention | 2.10 | $2.7 \times 10^9$ | $2.0 \times 10^8$ |
| Strain isolated from MYCOTAL | 1.54 | $3.0 \times 10^8$ | $4.1 \times 10^7$ |

As a result of the test, the followings have been found. The colony radiuses of the strain of the invention were 1.4 times (1.9 times on the area basis) longer than the colony diameter of the MYCOTAL strain, and a significant difference between both strains was found (t-test, $p<0.05$). In addition, regarding the total number of conidia in one colony, the strain of the invention was about 9 times higher than the MYCOTAL isolated strain, and a significant difference between both strains was found (t-test, $p<0.05$). In addition, the concentration of conidia in one colony of the strain of the invention was about 4.8 times larger than that of the MYCOTAL isolated strain, and a significant difference was found (t-test, $p<0.05$). From this test, it was found that the strain of the invention has superiority to the existent strain in the reproduction rate and concentration of conidia.

Test Example 5

Test for Effectiveness of the Strain of the Invention on *Frankliniella occidentalis*

After investigating the number of larvae of *Frankliniella occidentalis* living upon an eggplant (variety: Senryo-2) planted into three pots having a diameter of 17 cm, a spraying liquid comprising the strain of the invention was diluted and adjusted with water to give a conidia concentration of $5.0 \times 10^7$ (conidia/ml) (conidia suspension, within 2 hours after the preparation) and sprayed on all of the leaves in a sufficient amount using an automatic sprayer (NZ-2, manufactured by Sakata). Three pots after spraying were put in a greenhouse and kept under high humidity conditions for about 15 hours, and then the greenhouse was regulated in a general method. The number of larvae living upon all of the eggplant leaves was investigated 7 days after the spraying. The test results are shown in Table 4. In this connection, as a plot without treatment for comparison, the same test was carried out by spraying water instead of the spraying liquid. While the number of larvae was increased to about 1.4 times in the plot without treatment, it was reduced to about ⅓ in the plot with treatment. Accordingly, the controlling effect was confirmed.

TABLE 4

| Test plots | Test strains | Spraying concentration (conidia/ml) | The number of larvae (larvae) Before spraying | The number of larvae (larvae) After 7 days |
|---|---|---|---|---|
| Plot with treatment | Strain of the invention | $5.0 \times 10^7$ | 27 | 9 |
| Plot without treatment | No strain | 0 | 28 | 38 |

Test Example 6

Test for Effectiveness of the Strain of the Invention on *Trialeurodes vaporaiorum*

(1) Two pots having a diameter of 7 cm in which a one leaf stage kidney bean (variety: Shinedogawa natane) planted were put in an insect case (260×340×340 mm) and adults of *Trialeurodes vaporaiorum* were allowed to lay eggs for 7 hours. Each pot in which eggs were produced in this manner was transferred into an insect room maintained at 23° C. under dark conditions for 8 hours per day and left to stand to grow *Trialeurodes vaporaiorum*. Ten days after the oviposition (*Trialeurodes vaporaiorum*: 1 and 2 instar larval stages), the number of larvae living on the kidney bean leaves was recorded.

(2) Using a spray gun, a spraying liquid which had been diluted and adjusted to a given concentration (conidia concentration: two kind of densities of $1.0 \times 10^6$/ml and $1.0 \times 10^7$/ml) was sprayed once on the foliage parts of the kidney bean on each pot in such a manner that the amount of sprayed water became 10 ml per 1 pot. The conidia suspension was used within 2 hours of the preparation. Immediately after the spraying, they were transferred into a lidded plastic container (kept at 100% humidity, the bottom part was filled with water) and left to stand for 15 hours at 23° C. under a dark condition. Thereafter, the kidney bean leaves were left to stand in insects rooms under the same conditions as (1).

(3) Using a stereoscopic microscope, life or death of *Trialeurodes vaporaiorum* was judged to calculate the death rate 3 days after the spraying treatment of the liquid (*Trialeurodes vaporaiorum*: post-emergence). The test results are shown in Table 5.

TABLE 5

| Test strains | Spraying concentration (conidia/ml) | Death rate (%) After 3 days |
|---|---|---|
| Strain of the invention | $3.0 \times 10^6$ | 28 |
| Strain of the invention | $3.0 \times 10^7$ | 43 |
| No treatment | 0 | 5 |

Next, formulation examples of the invention are described, but the formulation amounts, formulation types and the like in the invention are not limited to only the described examples.

Formulation Example 1

About $10^{12}$ of conidia of the strain of the invention were suspended in 10 liters of distilled water and mixed with 100 g of Celite and 10 g of lactose were added thereto, followed by drying with a spray drier. As a water holding substance, 50 g of polyvinyl alcohol is added thereto to prepare a dust.

Formulation Example 2

Into a glass bottle, 85.0% by weight of liquid paraffin and 0.5% by weight of polyoxyethylene fatty acid ester are put and thoroughly mixed. To the obtained mixture, 10.0% by weight of the dust of the strain of the invention obtained in Formulation Example 1 is added and then mixed to obtain an oil flowable.

While the invention has been described in detail and with reference to specific embodiments thereof, it will be apparent to one skill in the art that various changes and modifications can be made therein without departing from the sprit and scope thereof.

This application is based on Japanese patent application (JP 2008-206866) filed on Aug. 11, 2008, the entire contents of which are incorporated hereinto by reference.

All references cited herein are incorporated in their entirety.

Industrial Applicability

When the strain of the invention is used, pests can be controlled markedly efficiently. Since the strain of the invention is excellent in propagation ability, it can ensure a high cell concentration and also maintain an excellent insecticidal effect. Based on this, efficient pest control becomes possible. Also, since it exhibits the insecticidal effect on the egg stage of pests, it becomes possible to carry out efficient pest control at early stage. In addition, since the invention uses a filamentous fungus, it also has a markedly high safety for the environment and is also useful in the case of controlling a pest for which fast-acting property and sustained effect are required.

The invention claimed is:

1. An biologically pure culture of *Lecanicillium muscarium* strain V-5. FERM BP-11135.

2. A method for controlling a pest selected from the group consisting of whiteflies, aphids, spider mites, thrips, rust mites, leaf miners, Pyralidae, cabbage moths and longhorn beetles comprising applying to the pest a pesticidally effective amount of the strain of claim 1.

3. The method according to claim 2, wherein the pest is whiteflies.

4. The method according to claim 2, wherein the pest is thrips.

* * * * *

UNITED STATES PATENT AND TRADEMARK OFFICE
CERTIFICATE OF CORRECTION

PATENT NO.        : 8,535,932 B2
APPLICATION NO.   : 13/058366
DATED             : September 17, 2013
INVENTOR(S)       : Satoshi Araki et al.

Page 1 of 1

It is certified that error appears in the above-identified patent and that said Letters Patent is hereby corrected as shown below:

In the claims:

Col. 10, line 20, Claim 1, line 1: "An" biologically pure culture

Delete "An"

Insert --A--

Col. 10, line 24, Claim 2, line 3: "Pyralidae"

Delete "Pyralidae"

Insert --*Pyralidae*--

Signed and Sealed this
Fourteenth Day of January, 2014

Michelle K. Lee
*Deputy Director of the United States Patent and Trademark Office*